US007575738B2

(12) United States Patent
Syud et al.

(10) Patent No.: US 7,575,738 B2
(45) Date of Patent: Aug. 18, 2009

(54) HEAT SHOCK PROTEIN AS A TARGETING AGENT FOR ENDOTHELIUM-SPECIFIC IN VIVO TRANSDUCTION

(75) Inventors: Faisal A. Syud, Clifton Park, NY (US); Ming Zhao, Clifton, NY (US); Andrew S. Torres, Clifton, NY (US)

(73) Assignee: General Electric Company, Niskayuna, NY (US)

( * ) Notice: Subject to any disclaimer, the term of this patent is extended or adjusted under 35 U.S.C. 154(b) by 674 days.

(21) Appl. No.: 10/917,326

(22) Filed: Aug. 13, 2004

(65) Prior Publication Data

US 2006/0034761 A1 Feb. 16, 2006

(51) Int. Cl.
*A61K 51/00* (2006.01)
*A61M 36/14* (2006.01)
(52) U.S. Cl. ............ 424/1.69; 424/1.81; 424/1.85; 424/1.89
(58) Field of Classification Search ........... 424/1.11, 424/1.65, 1.69, 9.1, 9.2, 9.3, 9.4, 9.5, 9.6, 424/9.7, 9.8; 530/350; 562/516
See application file for complete search history.

(56) References Cited

U.S. PATENT DOCUMENTS

| 4,752,141 | A |   | 6/1988 | Sun et al. ............. 374/161 |
| 4,986,671 | A |   | 1/1991 | Sun et al. ............. 374/131 |
| 5,175,343 | A | * | 12/1992 | Fritzberg et al. ....... 560/145 |
| 5,217,456 | A |   | 6/1993 | Narciso, Jr. .......... 606/15 |
| 5,275,594 | A |   | 1/1994 | Baker et al. .......... 606/12 |

FOREIGN PATENT DOCUMENTS

WO   WO 02 067761   6/2002

OTHER PUBLICATIONS

Lee et al (1996), Plant Physiology, vol. 110, No. 1, pp. 241-248.*
Mansfield et al (1987), Plant Physiology, vol. 84, No. 4, pp. 1007-1017.*
Perdew (1988), Journal of Biological Chemistry, vol. 263, No. 27, pp. 13802-13805.*
Hernando et al (1997), European Journal of Biochemistry, vol. 243, Nos. 1/2, pp. 460-467.*
Arthur Agatston, M.D., et al., "Quantification of Coronary Artery Calcium Using Ultrafast Computed Tomography", *J. Am. Coll. Cardiol.* 1990, 15, pp. 827-832.
Edwin L. Alderman, M.D., et al., "Five-year Angiographic Follow-up of Factors Associated With Progression of Coronary Artery Disease in the Coronary Artery Surgery Study (CASS)", *J. Am. Coll. Cardiol.* 1993, 22, pp. 1141-1154.
John A. Ambrose, M.D., et al., "Angiographic Progression of Coronary Artery Disease and the Development of Myocardial Infarction", *J. Am. Coll. Cardiol.* 1988, 12, pp. 56-62.

William C. Little, "Can Coronary Angiography Predict The Site of Subsequent Myocardial Infarction in Patients With Mild-to-Moderate Coronary Artery Disease?", *Circulation*, 1988, 78, pp. 1157-1166.
J.A. Ambrose, M.D., In: Fuster, V. (Ed.). *Syndromes of Atherosclerosis: correlations of clinical imaging and pathology*. Armonk, NY: Futura Publishing Company, Inc., 1996, pp. 105-122.
C.R. Becker, et al., "Visualization and Quantification of Coronary Calcifications with Electron Beam and Spiral Computed Tomography", *Eur. Radiol.* 2000, 10, pp. 629-635.
B.H. Brundage, M.D., In: Fuster, V. (Ed.).*Syndromes of Atherosclerosis: correlations of clinical imaging and pathology*. Armonk, NY: Futura Publishing Company, Inc., 1996, pp. 417-427.
M.J. Budoff, M.D., et al., "Rates of Progression of Coronary Calcium by Electron Beam Tomography", *Am. J. Cardiol*, 2000, 86, pp. 8-11.
C. Carrington, "Could Coronary Calcium Sceening Prevent This?", *Diagnostic Imaging*, 2000, (April), pp. 48-53.
T.M. Doherty, et al., "Coronary Calcium: The good, the bad, and the uncertain", *Am. Heart J.* 1999, 137, pp. 806-814.
M.D. Cerqueira, "Current Status of Radionuclide Tracer Imaging of Thrombi and Antheroma", *Seminars Nucl. Med.* 1999, 29, pp. 339-351.
R.E. Dinsmore, S.M. Rivitz. In: Fuster, V. (Ed.). *Syndromes of Atherosclerosis: correlations of clinical imaging and pathology*, Armonk, NY: Futura Publishing Company, Inc., 1996, pp. 277-289.
M. Doyle, G. Pohost. In: Fuster, V. (Ed.). *Syndromes of Atherosclerosis: correlations of clinical imaging and pathology*. Armonk, NY: Futura Publishing Company, Inc., 1996, pp. 313-332.
R. Erbel, et al., "Electron-Beam Computed Tomography for Detection of Early Signs of Coronary Arteriosclerosis", *Eur. Heart J.* 2000, 21, 720-732.
A. Farb, et al., "Sudden Coronary Death: Frequency of Active Coronary Lesions, Inactive Coronary Lesions, and Myocardial Infarction", *Circulation*, 1995, 92, pp. 1701-1709.
Z.S. Galis, et al., Macrophage Foam Cells From Experimental Atheroma Constitutively Produce Matrix-Degrading Proteinases, *Pro. Acad. Sci. USA*, 1995, 92, pp. 402-406.
M. Goyen et al., "MR-Angiography: the role of contrast agents", *Eur. J. Radio.* 2000, 34, 247-256.
T.M. Grist, M.D., P.A. Turski, M.D. In: Fuster, V. (Ed.). *Syndromes of Atherosclerosis: correlations of clinical imaging and pathology*. Armonk, NY: Futura Publishing Company, Inc., 1996, pp. 333-362.
H. Ikeda et al., "Increased Soluble Form of P-Selectin in Patients With Unstable Angina", *Am. J. Cardiol*, 1990, 65, 1693-1696.
L. Iuliano, et al., "Preparation and Biodistribution of 99m technetium Labelled Oxidized LDL in man", *Atherosclerosis*, 1996, 126, pp. 131-141.
W.R. Janowitz, M.D., et al., "Differences in Prevalence and Extent of Coronary Artery Calcium Detected by Ultrafast Computed Tomographay in Asymptomatic Men and Women", *Am. J. Cardiol.*, 1993, 72, pp. 247-254.

(Continued)

*Primary Examiner*—D L Jones
(74) *Attorney, Agent, or Firm*—Jenifer E. Haeckl

(57) ABSTRACT

The present invention relates to the use of Heat Shock Proteins and fragments thereof as targeting ligand. The Heat Shock Protein may be labeled with imaging agents that are capable of binding lectin-like oxidized low-density lipoprotein (LOX-1) or may be attached to a therapeutic agent. The sequences are useful for the diagnosis and monitoring of diseases as well as means for internalizing signaling moieties and therapeutics.

17 Claims, 6 Drawing Sheets

OTHER PUBLICATIONS

J.C. Kaski, MD, et al., "Rapid Angiographic Progression of Coronary Artery Disease in Patents with Angina Pectoris", *Circulation*, 1995, 92, pp. 2058-2065.

M.V. Knopp, M.D., et al., "Contrast Agents for MRA: Future Directions", *J. Magn. Reson, Imaging*, 1999, 10, pp. 314-316.

D.N. Ku, et al., "Pulsatile Flow and Atherosclerosis in the Human Carotid Bifurcation", *Atherosclerosis*, 1985, 5, pp. 292-302.

M. Marmion, E. Deutsch. "Tracers and Contrast Agents in Cardiovascular Imaging: present and future", *J. Nucl. Biol. Med.*, 1996, 40, pp. 121-131.

A. Mazzone, M.D., et al., "Increased Expression of Neutrophil and Monocyte Adhesion Molecules in Unstable Coronary Artery Disease", *Circulation*, 19963, August, 88, No. 2, pp. 358-363.

E.R. McVeigh, "MRI of Myocardial Function: Motion Tracking Techniques", *Magn. Reson. Imaging* 1996, 14, No. 2, pp. 137-150.

G.H. Glover, Ph.D., R.J. Herfkens, M.D., "Research Directions in MR Imaging", *J. Radiology*, 1998, 207, No. 2, pp. 289-295.

J.F.M. Meaney, et al., "Pulmonary Magnetic Resonance Angiography", *J. Magn. Reson. Imaging*, 1999, 10, pp. 326-338.

J. Narula, M.D., et al., "Strategic Targeting of Atherosclerotic Lesions", *J. Nucl. Cardiol*, 1999, 6, pp. 81-90.

J. Narula, M.D., "POPE: Predicting Outcome By Plaque Evaluation", *Nucl. Med. Commun.* 2000, 21, pp. 601-608.

M.R. Patel, M.D., et al., "Preoperative Assessment of The Carotid Bifurcation", *Stroke*, 1995, 26, 1753-1758.

J.F. Polak, M.D., "Focus on Imaging at the American Heart Association Annual Meeting", Radiology, 2000, 216, pp. 323-324.

R. Ross, "The Pathogenesis of Atherosclerosis: a perspective for the 1990s", Nature, 1993, 362, pp. 801-909.

J.A. Rumberger, Ph.D., M.D., "Electron Beam CT and Coronary Calcium Score", Circulation 1998, 97, pp. 2095-2097.

A. Schmermund, M.D., et al., "Usefulness of Topography of Coronary Calcium by Electron-Beam Computed Tomography in Predicting the Natural History of Coronary Atherosclerosis", *Am. J. Cardio.* 2000, 86, pp. 127-132.

A. Shaish, et al., "Imaging of Aortic Atherosclerotic Lesions by 125 I-LDL, 125 I-Oxidized-LDL, 125 I-HDL and 125 I-BSA", *Pathobiology*, 2001, 69, pp. 225-229.

D. Steinberg, "Low Density Lipoprotein Oxidation and its Pathobiological Significance", *J. Biol. Chem*, 1997, 272, pp. 29063-29066.

J-F Toussaint, M.D., et al., "T2-Weighted Contrast for NMR Characterization of Human Atherosclerosis", *Anterioscler Throb Vasc Biol*, 1995, 15, No. 10, pp. 1533-1542.

J-F Toussaint, M.D., et al., "Magnetic Resonance Images Lipid, Fibrous, Calcified, Hemorrhagic, and Thrombotic Components of Human Atherosclerosis In Vivo", *Circulation* 1996, 94, pp. 932-938.

S. Tsimikas, et al., "In Vivo Uptake of Radiolabeled MDA2, an Oxidation-Specific Monoclonal Antibody, Provides an Acc. Meas. of Atherosclerotic Lesions Rich in Oxidized LDL and Is Highly Sensitive to Their Regression", *Anterioscler Throb Vasc Biol*, 2000, 689-697.

S. Vallabhajosula, V.J. Fuster, "Atherosclerosis: Imaging Techniques and the Evolving Role of Nuclear Medicine", *J. Nucl. Med.* 1997, 38, pp. 1788-1796.

J. Weinberger, M.D., et al., "Morphologic and Dymanic changes of Atherosclerotic Plaque at the Carotid Arthery Bifurcation: Sequential Imaging by Real Time B-Mode Ultrasonography", *J. Am. Med. Assoc.* 1995, 12, pp. 1515-1521.

L. Wexler, M.D., et al., "Coronary Artery Calcification: Pathophysiology, Epidemiology, Imaging Methods, and Clinical Implications", *Circulation*, 1996, 94, pp. 1175-1192.

P. Wunderbalinger, et al., "Tat Peptide Directs Enhanced Clearance and Hepatic Permeability of Magnetic Nanoparticles", *Bioconjugate Chemistry*, 2002, 13, 264-268.

C. Yuan, Ph.D, et al., "Techniques for High-Resolution MR Imaging of Atherosclerotic Plaque", *J. Magn. Reson, Imaging*, 1994, 4, pp. 43-49.

C. Prodromou, et al., "Identification and Structural characterization of the ATP/ADP-Binding Site in the Hsp90 Molecular Chaperone", *Cell*, 1997, 90, pp. 65-75.

D.E. Feldman, J. Frydman, "Protein Folding in vivo: the importance of molecular Chaperones", Current Opinion in Structural Biology, 2000, 10, pp. 26-33.

Y. Delmeste, et al., "Involvement of LOX-1 in Dendritic Cell-Mediated Antigen Cross-Presentation", Immunity, 2002, 17, pp. 353-362.

K.M. Flaherty, "Structural Basis of the 7—Kilodalton Heat Shock Cognate Protein ATP Hydrolytic Activity", J. Biological Chem, 1994, 269, pp. 12899-12907.

H. Sondermann, et al., "Structure of a Bag/Hsc70 Complex: Convergent Functional Evolution of Hsp70 Nucleotide Exchange Factors", Science, vol. 291, Feb. 23, 2001, pp. 1553-1557.

J. Osipiuk, et al, "Streptococcus pneumonia YLxR at 1.35 A shows a putative new fold," Acta Cyst, 2001 D57, pp. 1747-1751.

\* cited by examiner

Figure 1

N-terminal
daaknqvaln pqntvfdakr ligrkfgdpv vqsdmkhwpf
qvindgdkpk vqvsykgetk afy
peeissm vltkmkeiae aylgypvt
d sqrqatkdag viaglnvlri ineptaaaia ygldr
tgkge rnvlifdlgg gtfdvsilti ddgifevkat agdthlg
ged fdnrlvnhfv eefkrkhkkd
isqnkravrr lrtacerakr tlss
stqasl eidslfegid fytsit
rarf eelcsdlfrs tlepvekalr dak
ldkaqih dlvlvggstr ipkvqkllqd ff
ngrdlnks inpdeavayg aavqaailmg

Figure 2

C-terminal mgdksenvqd lllldvapls lgletaggvm
talikrnsti ptkqtqiftt ysdnqpgvli
ysdnqpgvli qvyegeramt kdnnllgrfe
kdnnllgrfe lsgippapgv pqievtfdid
pqievtfdid angilnvtat dkstgkanki
dkstgkanki titndkgrls keeiermvqe
keeiermvqe aekykaedev qrervsakna
qrervsakna lesyafnmks avedeglkgk
avedeglkgk iseadkkkvl dkcqeviswl
dkcqeviswl dantlaekde fehkrkeleq
fehkrkeleq vcnpiisgly qgaggpgpgg
qgaggpgpgg fgaqgpkggs gsgptieevd
kkgg-lsgippap

Figure 3

1   mtfddlkiqt  vkdqpdeksn  gkkakglqfl  yspwwclaaa  tlgvlclglv vtimvlgmql 61   sqvsdlltqe  qanlthqkkk  legqisarqq  aeeasqesen  elkemietla rklnekskeq 121  melhhqnlnl  qetlkrvanc  sapcpqdwiw  hgencylfss  gsfnweksqe kclsldakll 181  kinstadldf  iqqaisyssf  pfwmglsrrn  psypwlwedg  splmphlfrv rgavsqtyps 241  gtcayiqrga  vyaencilaa  fsicqkkanl  raq

HEAT SHOCK PROTEIN AS A TARGETING AGENT FOR ENDOTHELIUM-SPECIFIC IN VIVO TRANSDUCTION

BACKGROUND OF THE INVENTION

1. Field of the Invention

Embodiments of the invention relate to compounds, compositions and methods of using Heat Shock Proteins for delivery and internalization of signaling agents and therapeutics. For instance, Heat Shock Protein 70 bind to a LOX-1 receptor and signal the LOX-1 receptor to transduce the HSP and any attached moiety across the endothelium. Therefore embodiments of the invention are useful for delivering various agents one desires to have internalized into a cell such as therapeutics and contrast/imaging agents. The isolated peptides may be attached either directly or through a linker to an imaging agent or a therapeutic. The compositions are also useful in delivering biological molecules to sites in vivo having high concentrations of oxidized low-density lipoprotein receptor (LOX-1 or OLR-1), including macrophages and other inflammatory cells. The contrast/imaging agents may be selected for various imaging modalities, more particularly the moieties are useful for imaging sites vulnerable to plaques associated with inflammation, such as atherosclerosis. The compositions are useful for the diagnosis and monitoring of inflammation and diseases in which inflammation plays a role such as various cardiovascular diseases including but not limited to atherosclerosis, vulnerable plaque and coronary artery disease as well as rheumatoid arthritis.

2. Description of Related Art

HSPs (Heat Shock Proteins) are a family of highly conserved proteins found in the cells of all organisms, from bacteria to mammals. HSPs are required for cellular metabolism even in unstressed cells. They facilitate the synthesis, structure, transport, and other aspects of protein assembly such as helping newly synthesized polypeptides fold and thus prevent premature interactions with other proteins (i.e. act as chaperones). HSP expression increases in response to physiological stresses such as a rise in temperature, altered pH and oxygen deprivation. These stresses may result in a break down of three-dimensional structure or unfolding of a cell's proteins. If the stress is left unchecked the mis-folded or unfolding proteins form aggregates that may eventually kill the cell. HSPs bind to damaged proteins helping them refold into their proper shapes and/or prevent the damage from occurring.

EP 1 046 652 A1 discloses a fusion polypeptide composed of an extracellular domain of mammalian oxidized-LDL receptor (LOX-1) and a part of IgG, whereby the fusion polypeptide may be labeled with a labeling agent. Thus, the fusion polypeptide can be used to detect, quantify, separate, and purify oxidized LDL. The fusion polypeptides can not be used to detect or quantify LOX-1.

The TAT peptide sequence and the recently reported Antp internalization sequence have demonstrated internalization activity of various substrates both in vitro and in vivo. Neither has been demonstrated to target a specific receptor for the purpose of delivering a diagnostic contrast agent to a diseased area on the endothelium, though TAT peptide has been used to non-specifically deliver iron oxide nanoparticles into cells (Wunderbalinger, P. et al., *Bioconjugate Chemisfry*, 2002, 13, 264-8). A disadvantage of these schema is the non-specificity of the peptides for targeting of the contrast agent to the cells of interest. The non-specific delivery of contrast agent would significantly deride attempts to distinguish areas of diagnostic interest (i.e. atherosclerotic lesions) from other functional areas of the vasculature.

Cardiovascular diseases are the leading cause of death in the United States, accounting annually for more than one million deaths. Atherosclerosis is the major contributor to coronary heart disease and is a primary cause of non-accidental death in Western countries (Coopers, E. S. Circulation 1993, 24, 629-632; WHO-MONICA Project. Circulation 1994, 90, 583-612). It is well-documented that multiple risk factors contribute to atherosclerosis such as hypertension, elevated total serum cholesterol, high levels of low density lipoprotein (LDL) cholesterol, low levels of high density lipoprotein (HDL) cholesterol, diabetes mellitus, severe obesity, and cigarette smoking (Orford et al., *Am. J. Cardiol.* 2000, 86 (suppl.) 6H-11H). Considerable effort has been made in defining the etiology and potential treatment of atherosclerosis and its consequences, including myocardial infarction, angina, organ failure and stroke. To date, treatment of atherosclerosis focuses on lowering cholesterol levels and modifying lipids. However, recent studies indicate that 40% of deaths due to coronary disease occurred in men with total cholesterol levels of below 220 mg/dl. (Orford et al). There are many unanswered questions including how and when atherosclerotic lesions become vulnerable and life-threatening, the best point of intervention, and how to detect and monitor the progression of lesions.

Several invasive and noninvasive techniques are routinely used to image atherosclerosis and to assess the progression and stabilization of the disease. These include coronary angiography, intravascular ultrasound angioscopy, intravascular magnetic resonance imaging, and thermal imaging of plaque using infrared catheters. These techniques have been used successfully to identify vulnerable plaques. However, these techniques are generally invasive, requiring surgery, insertion of probes, cameras, or other invasive procedures. For instance, soluble markers, such as P-selectin, von Willebrand factor, Angiotensin-converting enzyme (C 146), C-reactive protein, D-dimer (Ikeda et al., Am. J. Cardiol., 1990, 65, 1693-1696), and activated circulating inflammatory cells are found in patients with unstable angina pectoris however, their presence cannot be used to locate the involved lesion. Temperature sensing elements contained in catheters have been used for localizing plaque on the theory that inflammatory processes and cell proliferation are exothermic processes and are described for example in U.S. Pat. No. 4,986,671 and U.S. Pat. No. 4,752,141. An angiogram reflects luminal diameter and provides a measure of stenosis with excellent resolution, however, it does not image the vessel wall or the various histopathological components.

Techniques currently available typically identify some of the morphological and/or functional parameters of atherosclerosis and provide qualitative or semiquantitative assessment of the relative risk associated with the disease. However, these diagnostic procedures are either invasive or yield little information on the underlying pathophysiology such as cellular composition of the plaque, and biological characteristics of each component in the plaque at the molecular level. For further discussion of inflammatory related conditions and diseases see co-pending U.S. application Ser. Nos. 10/691,532 and 10/691,533 which are hereby incorporated by reference in their entirety.

Oxidized LDL (oxLDL) is strongly implicated in the pathobiology of atherosclerosis. It is suspected that the lipid pool in atherosclerotic plaque is due to uptake of oxLDL, not native LDL. OxLDL is recognized by scavenger receptors on macrophages; uptake of large quantities of oxLDL by macrophages can give rise to foam cells which are an important component of atherosclerotic plaque. LOX-1 or lectin-like oxidized LDL receptor was recently identified as a receptor on endothelial cells for oxLDL; it mediates the internalization of oxLDL by endothelial cells and is distinct from macrophage scavenger receptors such as those described in WO 2002/06771, (Sawamura, T. *Nature* 1997 386:73-77). The amino acid sequence of LOX-1 is shown in FIG. 3. LOX-1 also is expressed on macrophages and may play a role in oxLDL recognition/internalization on these cells (Yoshida, H. et al., *Biochem. J.* 1998 334:9-13). LOX-1 is nearly undetectable in healthy human aorta samples but is found in atherosclerotic plaque, particular early lesions that are unlikely to be detectable by other means (Kataoka, H. et al., *Circulation* 1999 99:3110-3117). Recent work suggests that recognition of oxLDL by LOX-1 is a critical early step in expression of adhesion receptors on endothelial cells. These receptors are believed to be responsible for attracting monocytes to the early atherosclerotic plaque.

As such, a non-invasive method to diagnose and monitor various cardiovascular diseases (e.g., atherosclerosis, vulnerable plaque, coronary artery disease, renal disease, thrombosis, transient ischemia due to clotting, stroke, myocardial infarction, organ transplant, organ failure and hypercholesterolemia) is needed. The non-invasive method should yield information regarding the underlying pathophysiology of the plaque, such as the cellular composition of the plaque and biological characteristics of each component in the plaque at the molecular level.

The description herein of disadvantages and deleterious properties and/or results achieved with known products, methods, and apparatus, is in no way intended to limit the scope of embodiments of the invention. Indeed, the present embodiments of the invention may utilize one or more known products, methods, and apparatus without suffering from the described disadvantages and deleterious properties and/or results.

SUMMARY OF THE INVENTION

Embodiments of the invention are directed to the use of a HSP or portions thereof that are useful for internalizing agents into cells, including but not limited to, therapeutics and signaling agents. In another embodiment the binding portions of HSP provide a useful means for identifying and localizing inflammation in the body, such as inflammation associated with atherosclerosis. Embodiments of the invention additionally provide methods of using HSP (LOX-1 peptide binding sequences) to assist in diagnostic procedures. More particularly, the compounds and compositions are used in methods for detecting the formation of plaques. Embodiments of the invention additionally provide for methods of using LOX-1 peptide binding sequences to treat human and/or other animal diseases caused by over expression or heightened expression of LOX-1.

There is a need to develop an imaging agent/molecule complex that is capable of binding LOX-1 and being imaged by external non-invasive imaging techniques. There also is a need to develop a method of making such an imaging agent/molecule complex, as well as a method of imaging a subject to assess the presence of a disease or lesion in a patient or the risk of the patient having the disease or lesion in the future. Diseases envisioned include: atherosclerosis, vulnerable plaque, coronary artery disease, renal disease, thrombosis, transient ischemia due to clotting, stroke, myocardial infarction, organ transplant, organ failure and hypercholesterolemia. It therefore is a feature of embodiments of the invention to provide an imaging agent/molecule that is capable of binding LOX-1 in vivo to enable the detection of, and hence, quantitation of the expression of the LOX-1 protein.

In addition to the imaging purposes, the compounds and compositions also may be used as a delivery mechanism for biological molecules that may be of interest in areas with high concentration of LOX-1, such as macrophages and other inflammatory cells.

In accordance with these and other features of various embodiments of the invention, there is provided a compound of formula I: $[S-(L)_n-H]$, wherein S is a signal providing structural unit that provides a signal that can be detected in vivo or detected in vitro, L links S to H, H is a Heat Shock Protein (HSP) that binds to LOX-1, and n is either 0 or 1. Another feature of embodiments of the invention is a compound having the formula II: $[T-(L)_n-H]$, wherein T is a therapeutic agent, L links T to H, H is HSP that binds to LOX-1, and n is either 0 or 1. Another feature of embodiments of the invention is a compound of the formula I further comprising the attachment of a therapeutic agent, T, in addition to the existing signaling unit allowing for both delivery of the therapeutic and the ability to image and quantify the delivery.

Another feature of embodiments of the invention is a composition comprising a compound of formula I: $[S-(L)_n-H]$, wherein S is a signal providing structural unit that provides a signal that can be detected in vivo or detected in vitro, L links S to H, H is a Heat Shock Protein (HSP) that binds to LOX-1, and n is either 0 or 1 and a pharmaceutically acceptable excipient. Another feature of embodiments of the invention is a composition comprising compound having the formula II: $[T-(L)_n-H]$, wherein T is a therapeutic agent, L links T to H, H is HSP that binds to LOX-1, and n is either 0 or 1 and a pharmaceutically acceptable excipient. Another feature of embodiments of the invention is a composition comprising a compound of the formula I and a pharmaceutically acceptable excipient further comprising the attachment of a therapeutic agent, T, in addition to the existing signaling unit allowing for both delivery of the therapeutic and the ability to imagine and quantify the delivery. Another feature of embodiments of the invention is a kit comprising the compositions of formula I and formula II.

Another feature of embodiments of the invention is a method of imaging a tissue or cell culture to detect the presence and/or amount of LOX-1, comprising delivering a compound of formula I, optionally attached to a therapeutic; optionally delivering or washing with a clearing agent to remove compound that is not bound to LOX-1; and imaging the tissue or cell culture to detect the signal generated by S and thereby detect the presence and/or amount of LOX-1. Another feature of embodiments of the invention is a method to detect the presence and/or amount of LOX-1 in vivo, comprising administering to a mammal a compound formula I, optionally attached to a therapeutic; optionally administering a clearing agent to remove compound that is not bound to LOX-1; and subjecting the mammal to imaging effective to detect the signal generated by S to thereby detect the presence and/or amount of LOX-1. Another feature of embodiments of the invention is a method of detecting and quantifying LOX-1 in a mammal comprising administering the above-described composition to a mammal suspected of a disease or disorder caused by expression of LOX-1, imaging the mammal, and detecting the presence and relative quantity of LOX-1 in the imaged area. The method also includes repeating the above procedure periodically to monitor the quantity of LOX-1, thereby monitoring the efficacy of therapies for treating diseases or disorders caused by expression of LOX-1.

Another feature of embodiments of the invention is a method of monitoring the efficacy of therapies for treating inflammatory diseases, such as atherosclerosis comprising administering to a mammal the compound formula I or formula II; optionally administering a clearing agent to remove the compound that is not bound to LOX-1; subjecting the mammal to imaging effective to detect the signal generated by S to thereby detect the amount of LOX-1; and repeating the administration and imaging procedures at least once over a period of time to detect the difference in amount of LOX-1.

In another embodiment, the invention provides methods for determining the expression levels of LOX-1 in mammals suspected of a disease or disorder caused by expression of LOX-1.

These and other features of the embodiments of the invention will be readily apparent to those skilled in the art upon reading the detailed description that follows.

BRIEF DESCRIPTION OF THE DRAWINGS

FIG. 1 is the amino acid sequence for the N-terminal homolog of HSP-70.

FIG. 2 is the amino acid sequence for the C-terminal homolog of HSP-70.

FIG. 3 is the amino acid sequence for human LOX-1.

DETAILED DESCRIPTION OF PREFERRED EMBODIMENTS

Figure 4:
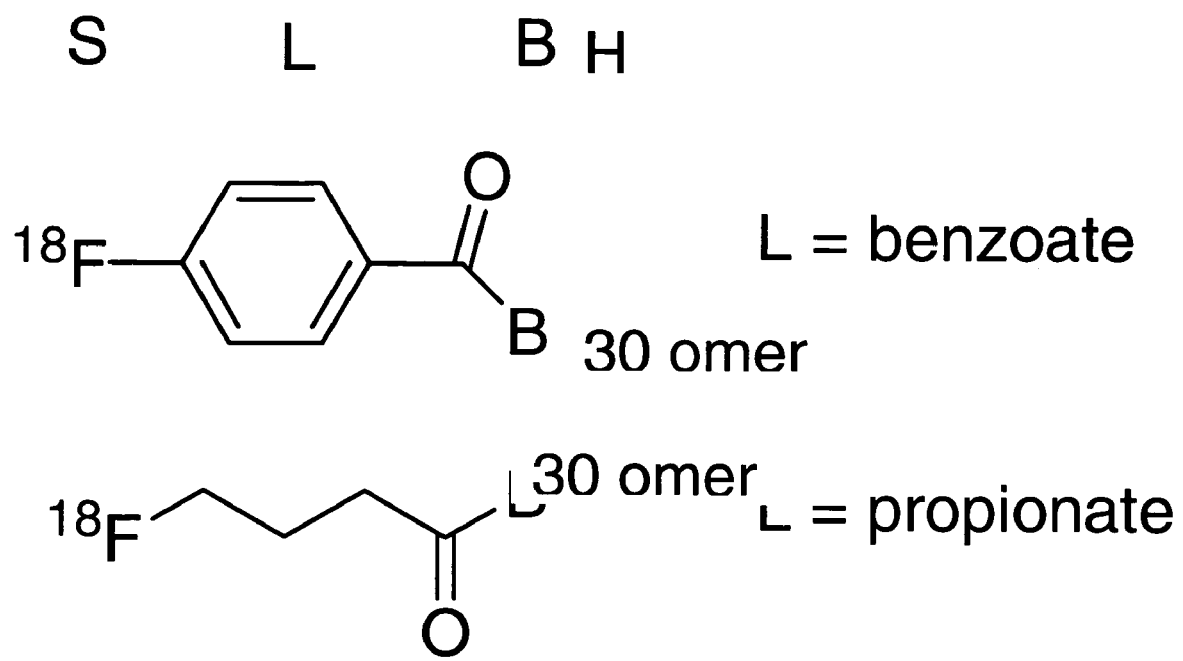
FIG. 4 is an illustration of L and S variation in the S-L-H compound.
Figure 5:
FIG. 5 is an illustration of the tertiary structure for the N-terminal homolog of HSP-70.
Figure 6:
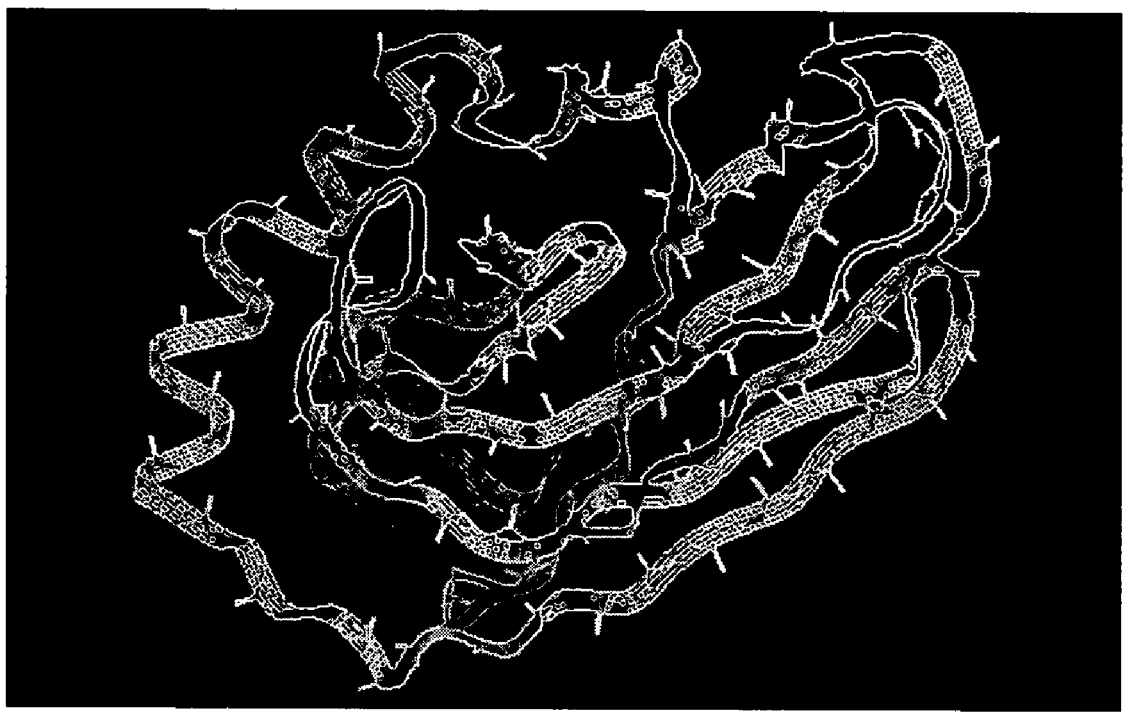
FIG. 6 is an illustration of the tertiary structure for the C-terminal homolog of HSP-70.

Embodiments of the invention are not limited to the particular methodology, protocols, cell lines, and reagents described in the preferred embodiments, as these may vary. It also is to be understood that the terminology used herein is for the purpose of describing particular embodiments only, and is not intended to limit the scope of any embodiment of the invention.

LOX-1 or lectin-like oxidized LDL receptor was recently identified as a receptor on endothelial cells for oxLDL; it mediates the internalization of oxLDL by endothelial cells and is distinct from macrophage scavenger receptors such as those described in WO 2002/06771, (Sawamura, T. *Nature* 1997 386:73-77). LOX-1 also is expressed on macrophages and may play a role in oxLDL recognition/internalization on these cells (Yoshida, H. et al., *Biochem. J.* 1998 334:9-13). LOX-1 is nearly undetectable in healthy human aorta samples but is found in atherosclerotic plaque, particular early lesions that are unlikely to be detectable by other means (Kataoka, H. et al., *Circulation* 1999 99:3110-3117). An antibody to LOX-1 has been described as being useful to treat atherosclerosis by preventing binding of oxLDL to LOX-1 (WO164862). Recent work suggests that recognition of oxLDL by LOX-1 is a critical early step in expression of adhesion receptors on endothelial cells. These receptors are believed to be responsible for attracting monocytes to the early atherosclerotic plaque. The monocytes penetrate the endothelial, differentiate into macrophages and can end up as foam cells in the growing plaque. Finally, peptides were developed that bind to LOX-1 using phage display technology (White, S. et al., *Hypertension* 2001 37:449-455).

Various species of LOX-1 have been isolated and sequenced revealing relatively significant dissimilarity interspecies (Chen, M., et al., *J. Biochem.*, 355:289-95 (2001). U.S. Pat. Nos. 5,962,260 and 6,197,937, the disclosures of which are incorporated by reference herein in their entirety, disclose the amino acid sequences of human and bovine LOX-1. Using the techniques disclosed in these documents, and the guidelines provided herein, those skilled in the art are capable of isolating LOX-1 from any species and creating molecules that bind to the human LOX-1.

Thus, the moiety that binds to LOX-1 can be synthesized using known techniques, given the known amino acid sequence of the LOX-1 polypeptide. Moieties that bind only specific portions of LOX-1 also can be synthesized given the known and/or expected antigenic determinant or epitope binding site. Unlike known moieties that bind to LOX-1, the inventive moieties are designed to bind to LOX-1 in the presence of human fluids (in vivo or in vitro) with sufficient specificity such that tissue in which LOX-1 has been overexpressed (e.g., atherosclerotic tissue) may be differentiated from healthy tissue. The inventive molecules also are bound, again in the presence of human fluids, to a signal moiety with sufficient specificity to enable detection using imaging techniques or to a pharmaceutical to provide therapeutic relief.

A number of methods can be used to screen and evaluate the binding affinity of different ligands. One method for example includes fluorescent based in vitro experiments. Cell-based assays can simultaneously yield information on the amount of signal generating entity necessary for detection, and therefore required for conjugation to ligands.

In the case of the peptidic ligands, a fluorescent dye preferably is attached to the N-terminus of the peptide via a flexible linker, such as the amino acid sequence KKGG (K=Lysine, G=Glycine). In the event that the N-terminus is linked to a signaling moiety with no further functional ends for dye attachment, the dye also can be attached via the side-chain amine of a K residue incorporated into the sequence (e.g. in the linker).

Regardless of the type of screening assay used, (e.g., a generic in vitro model), it first is assumed that the amount of LOX-1 on the surface of a substrate is known, whether it be cells or some other substrate. In a multi-well transparent plate, LOX-1 is present (either as pure LOX-1 protein or expressed on cells) uniformly across the wells. Labeled ligands then can be added and incubated for an optimized amount of time in the different wells. The wells then are washed thoroughly with a buffer, such as Phosphate buffered saline (PBS), and the plate then imaged while shining a laser to excite and initiate fluorescence of the dye attached to the ligands. The fluorecent intensity from each well, and thus the degree of different ligand binding, can be quantified. To obtain the absolute number of ligand bound, the signal preferably is further calibrated by obtaining the fluorescent intensity of a known quantity of dye-conjugated ligand under similar conditions of the binding assay. If the number of LOX-1 molecule is known, and the amount of bound ligands determined, dissociation constants to evaluate ligand-binding affinity can be calculated. Different ligands can thus be screened quantitatively for their binding affinity. The number of bound ligands per cells also is capable of providing information on parameters required to obtain a detectable signal from a signal-generating entity conjugated to the ligands.

Images in the assay may be acquired using a laser confocal microscope or an Imager. For example, images of peptides bound to cells can be obtained using a laser confocal microscope as follows: HCAE cells can be grown on high quality borosilicate 8-chambered glass slides (Electron Microscopy Sciences, Fort Washington, Pa.). Then, about 10 µL of 1 mg/ml of an aqueous solution of a labeled peptide can be added to the cells and incubated for 1 hour. Subsequently, the cells preferably are washed with HBSS buffer three times. The cells then can be fixed with 4% formaldehyde solution over 10 minutes. After a final wash with buffer, the slide is imaged. Images preferably are acquired using an OLYMPUS laser scanning confocal microscope, model Fluoview 300, using Ar-ion laser (selecting 488 nm line) and a 510-nm long-pass filter. Images can be acquired using two channels: reflected light and fluorescent mode channel, or an overlay of both channels. Further it is possible to research the level of internalization through, for instance, confocal microscopy. Confocal microscopy provides the ability to scan across three dimensions and thus probe into cell interiors as well as across a plane of cell-surface. Hence, whether a fluorescent agent has internalized or not may be investigated.

For higher throughput screening the method described above can be extended: a 96-well plate may replace the 8-well slides and a Biorad Imager, model FX Proplus, replace the confocal microscope. For example, images of fluorescein-labeled HSP bound to cells can be obtained using an Imager, whereby HCAE cells can be laid on and grown in wells on a standard commercial 96-well plate (Becton-Dickenson, Franklin Lakes, N.J.). Then, about 10 μL of 1 mg/ml labeled HSP aqueous solution can be added to the cells and incubated for 1 hour. Subsequently, the cells preferably are washed with PBS buffer three times. After a final wash with buffer, the slide can be imaged using the Biorad imager selecting "Fluorescein" as the fluorophore.

The labeled ligands can be used as a diagnostic to assist in imaging a targeted tissue that is suspected of overexpressing LOX-1. The method of diagnosis therefore includes first administering to a subject a composition containing the labeled ligand of the embodiment of the invention. The method also optionally includes administering a clearing agent to assist in clearing any unbound HSP from circulation. Depending on the particular label that has been labeled to the ligand, the appropriate imaging technique is employed to image the targeted tissue. For example, when $^{18}F$ is used as the labeling agent PET imaging is conducted.

The imaging method can be used as a diagnostic to detect the presence of LOX-1 in human tissue. In addition, the imaging method can be repeated over a number of days to provide a quantitative assessment of the degree of growth or expression of the LOX-1 polypeptide.

Embodiments of the invention also encompass a composition comprising the labeled ligands, as well as a kit for imaging a targeted tissue. The kit preferably comprises a composition comprising the labeled ligand of embodiments of the invention, or optionally, comprises two compositions; one containing an $^{18}F$ precursor, and the other containing the remaining portion of the labeled ligand. These two compositions can be mixed just prior to administration to the subject, thereby preserving the life of the $^{18}F$ radionuclide.

One embodiment of the invention relates to molecules useful in detecting or imaging tissue by binding to LOX-1. More preferably, the tissue may be associated with inflammation. More preferably the tissue is atherosclerotic tissue. The molecule complexes comprise a sequence moiety that binds to LOX-1 in the presence of human fluids with adequate specificity and contains a signal agent. In a preferred embodiment the molecule complexes comprise a sequence moiety that binds to LOX-1 in the presence of human fluids with adequate specificity such that inflammation tissue such as atherosclerotic tissue may be differentiated from healthy tissue; and contains a signal agent that can be detected.

Embodiments of the invention are directed to the use of a HSP or portions thereof which are useful for internalizing agents into cells including but not limited to therapeutics and signaling agents. The binding portions of HSP provide a useful means for identifying and localizing inflammation in the body, such as inflammation associated with atherosclerosis. Embodiments of the invention additionally provide methods of using HSP (LOX-1 peptide binding sequences) to assist in diagnostic procedures. More particularly, the compounds and compositions are used in methods for detecting the formation of plaques. Embodiments of the invention additionally provide for methods of using LOX-1 peptide binding sequences to treat human and/or other animal diseases caused by over expression or high expression of LOX-1.

In addition to the imaging purposes described herein, the compounds and compositions also may be used as a delivery mechanism for biological molecules that may be of interest in areas with high concentration of LOX-1, such as macrophages and other inflammatory cells.

In accordance with these and other features of various embodiments of the invention, there are provided a compound of formula I: $[S-(L)_n-H]$, wherein S is a signal providing structural unit that provides a signal that can be detected in vivo or detected in vitro, L links S to H, H is a Heat Shock Protein (HSP) that binds to LOX-1, and n is either 0 or 1. Another feature of the invention is a compound having the formula II: $[T-(L)_n-H]$, wherein T is a therapeutic agent, L links T to H, H is HSP that binds to LOX-1, and n is either 0 or 1. Another feature of the embodiment of the invention is a compound of the formula I further comprising the attachment of a therapeutic agent, T, in addition to the existing signaling unit allowing for both delivery of the therapeutic and the ability to image and quantify the delivery.

Another feature of an embodiment of the invention is a composition comprising a compound of formula I: $[S-(L)_n-H]$, wherein S is a signal providing structural unit that provides a signal that can be detected in vivo or detected in vitro, L links S to H, H is a Heat Shock Protein (HSP) that binds to LOX-1, and n is either 0 or 1 and a pharmaceutically acceptable excipient. Another feature of the embodiment of the invention is a composition comprising compound having the formula II: $[T-(L)_n-H]$, wherein T is a therapeutic agent, L links T to H, H is HSP that binds to LOX-1, and n is either 0 or 1 and a pharmaceutically acceptable excipient. Another feature of the embodiment of the invention is a composition comprising a compound of the formula I and a pharmaceutically acceptable excipient further comprising the attachment of a therapeutic agent, T, in addition to the existing signaling unit allowing for both delivery of the therapeutic and the ability to imagine and quantify the delivery. Another feature of the embodiment of the invention is a kit comprising the compositions of formula I and formula II.

Yet another feature of an embodiment of the invention is a method of imaging a tissue or cell culture to detect the presence and/or amount of LOX-1, comprising delivering a compound of formula I, optionally attached to a therapeutic; optionally delivering or washing with a clearing agent to remove compound that is not bound to LOX-1; and imaging the tissue or cell culture to detect the signal generated by S and thereby detect the presence and/or amount of LOX-1. Another feature of the embodiment of the invention is a method to detect the presence and/or amount of LOX-1 in vivo, comprising administering to a mammal a compound formula I, optionally attached to a therapeutic; optionally administering a clearing agent to remove compound that is not bound to LOX-1; and subjecting the mammal to imaging effective to detect the signal generated by S to thereby detect the presence and/or amount of LOX-1. Another feature of the embodiment of the invention is a method of detecting and quantifying LOX-1 in a mammal comprising administering the above-described composition to a mammal suspected of a disease or disorder caused by expression of LOX-1, imaging the mammal, and detecting the presence and relative quantity of LOX-1 in the imaged area. The method also includes repeating the above procedure periodically to monitor the quantity of LOX-1, thereby monitoring the efficacy of therapies for treating diseases or disorders caused by expression of LOX-1.

In accordance with another feature of an embodiment of the invention, there is provided a method of monitoring the efficacy of therapies for treating inflammatory diseases, such as atherosclerosis comprising administering to a mammal the compound formula I or formula II; optionally administering a clearing agent to remove the compound that is not bound to LOX-1; subjecting the mammal to imaging effective to detect the signal generated by S to thereby detect the amount of LOX-1; and repeating the administration and imaging procedures at least once over a period of time to detect the difference in amount of LOX-1.

In another embodiment the HSP (ligand) is bound to a signaling agent and/or a therapeutic and a targeting moiety wherein the targeting moiety, such as a cancer cell specific sequence is used to direct the signaling agent/therapeutic into the cell. The process may be repeated to increase the specific signal above background or to increase the amount of therapeutic delivered.

For each of the recited embodiments the Heat Shock Protein may be a full sequence, a variant, a fragment, or homologs thereof. Preferably the Heat Shock Protein is a Heat Shock Protein 70, a variant thereof, a fragment thereof, or homologs of either the full sequence or fragments thereof. More preferably the LOX-1 peptide binding sequence is a HSP-70 fragment. More preferably the Heat Shock Protein 70 fragments are 30 omers or shorter. More preferably the 30 omers are selected from between amino acid number 383 and 640.

For each embodiment of the invention S may be independently selected from a luminescent dye, a radionuclide, a near infrared dye, a magnetically active isotope, a superparamagnetic particle, a metal ion having a Z value of greater than 50, an encapsulated species, and combinations thereof. In one preferred embodiment S is selected from fluorescein, $^{11}$C, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd, $^{175}$Lu, superparamagnetic iron oxide nanoparticles, heavy metal ions, gas-filled microbubbles, optical dyes, porphyrins, texaphyrins, highly iodinated organic compounds chelates thereof, polymers containing at least one of the aforementioned components, endohedral fullerenes containing at least one of the aforementioned, and mixtures thereof.

In one embodiment the signaling agent is a luminescent dye which is fluorescein, or derivatives thereof. In another embodiment the signaling agent is a radionuclide which is a positron emitter which is $^{18}$F and $^{11}$C. In another embodiment the signaling agent is a radionuclide which is a gamma emitter. In another embodiment the signaling agent is an infrared dye. In another embodiment the signaling agent is a magnetically active isotope which is paramagnetic. In another embodiment the magnetically active isotope is an isotope of gadolinium. In another embodiment the signaling agent is a radionuclide which is a superparamagnetic particle which is a nanoparticle, preferably the nanoparticle comprises at least one of iron oxide and elemental iron. In another embodiment the signaling agent is an element having a Z value of greater than about 50, preferably the element is iodine or bismuth. In another embodiment the signaling agent is an encapsulated species, preferably the encapsulated species is selected from the group consisting of a micelle, a liposome, a polysome, and a gas-filled microbubble.

For each of the described embodiments L may be independently selected. In one embodiment the linker is an organic radical having a valence of at least 2. In one embodiment the organic radical is covalently bound to both group S and group H. In another embodiment the organic radical is ionically bound to one of group S and group H. In another embodiment the organic radical is ionically bound to both group S and group H. In another embodiment the organic radical comprises between 1 and about 10,000 carbon atoms. In another embodiment the organic radical is selected from an alkylene, arylene, cycloakylene, aminoaklylene, aminoarylene, aminocycloalkylene, thioalkylene, thioarylene, thiocycloalkylene, oxyalkylene, oxyarylene, oxycycloalkylene, acylalkylene, acylarylene, acylcycloalkylene units, and combinations thereof. In one embodiment the acylarylene unit is a 4-acylphenylene group having the following structure:

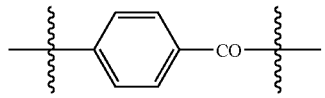

In another embodiment the organic radical is a metal chelating agent that binds at least one metal cation selected from the group consisting of cations of $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, 111In, 154-158Gd, and $^{175}$Lu. In another embodiment the metal chelating agent is selected from DTPA, 1,4,7-triaza-cyclononane-N,N',N"-triacetic acid (NOTA), p-bromoacetamido-benyl-tetraethylaminetetraacetic acid (TETA), 1,4,7,10-tetraazacyclododecanetetraacetic acid (DOTA), EDTA, CHXa.

Current imaging agents and modalities primarily provide anatomical information. The information is typically obtained through some form of contrast which may provide fairly high-resolution. However, underlying disease states are biochemical processes that propagate the disease far before the outward physical symptoms appear. Having the ability to image the biochemical pathways, or specific markers in the pathways (biomarkers), in the early disease process provides functional information. This may be termed targeted molecular imaging.

Contrast agent targeting a disease state can be achieved whereby the agent is bound to ligands that specifically identify and bind molecules that are over-expressed in a given disease state at the biological site of interest. A targeting agent will bind to a molecule, typically termed a "receptor," with high selectivity and specificity; the moiety on the agent that recognizes the receptor is the ligand. There is evidence demonstrating that receptors indicative of a particular disease state exist and may be used to image a disease. For instance, in the area of radiopharmaceuticals SPECT imaging is used.

Many small biomolecules have been synthesized, radiolabeled, and studied for their potential use as new diagnostic imaging agents for various diseases (Hom, R. K. et al., *Nucl. Med. Biol.* 1997, 24, 485; Liu, S. et al., *Bioconjugate Chem.* 1997, 8, 621; Goldsmith, S. J. *Semin. Nucl. Med.* 1997, 27, 85; Fischman, A. J. et al., *J. Nucl. Med.* 1993, 34, 2253; Fischman, A. J. et al., *Semin. Nucl. Med.* 1994, 24, 154; Reubi, J. C. *Q. J. Nucl. Med.* 1997, 41, 63; Signore, A. *Q. J. Nucl. Med.* 1995, 39, 83; Thakur, M. L. *Nucl. Med. Commun.* 1995, 16, 724; Lister-James, J.; Moyer, B. R.; Dean, R. T. *Q. J. Nucl. Med.* 1996, 40, 221; McAfee, J. G.; Neumann, R. D. *Nucl.*

Med. Biol. 1996, 23, 673). Examples of radiolabeled receptor ligands for receptor imaging include peptides, small molecules, and antibodies. Peptide ligands include $^{99m}$Tc labeled chemotactic peptides (Baidoo, K. E. et al., *J. Nucl. Med.* 1994, 35, 19P (abstract 67); Babich, J. W. et al., *J. Nucl. Med.* 1993, 34, 1964) leukotriene B4 LTB4 receptor antagonists (Rajopadhye, M. et al., *Abstracts of Papers*, 216th ACS National Meeting, Boston, Mass., 1998; American Chemical Society: Washington, DC, 1998; abstract 005 (medicinal chemistry); Barrett, J. A. et al., *J. Nucl. Med.* 1998, 39, 215P (abstract 957)), and tuftsin receptor antagonists (Goodbody, A. E. et al., *Eur. J. Nucl. Med.* 1994, 21, 790 (abstract 262)) for imaging focal sites of infection; somatostatin analogues (Maina, T. et al., *Eur. J. Nucl. Med.* 1994, 21, 437), bombesin analogues (Baidoo, K. E. et al., *Bioconjugate Chem.* 1998, 9, 218), folate receptor antagonists (Wang, S. et al., *Bioconjugate Chem.* 1997, 8, 673), vasoactive intestinal peptide (VIP; Kurtaran, A. et al., *J. Nucl. Med.* 1997, 38, 880) for imaging tumors, and platelet GPIIb/IIIa receptor antagonists for imaging thrombi (Barrett, J. A. et al., *J. Nucl. Med.* 1995, 36, 16P (abstract 55); Liu, S. et al., *Bioconjugate Chem.* 1996, 7, 63; Muto, P. et al., *J. Nucl. Med.* 1995, 36, 1384). Other radiolabeled receptor ligands such as neurotransmitter receptor antagonists, dopamine transporter antagonists, progestin receptor antagonists, and sigma receptor ligands have also been investigated (Hom, R. K. et al., 1997). Other examples include radiolabeled antibodies for diagnosis and therapy (Keenan, A. M. et al., *J. Nucl. Med.* 1985, 26, 531; Khaw, B. A.; Strauss, H. W.; Narula, J. *J. Nucl. Med.* 1993, 34, 2264), and $^{99m}$Tc-labeled target-specific small molecule radiopharmaceuticals (Hom, R. et al., 1997; Lister-James, J. et al., 1996). Beyond SPECT, targeted imaging using MRI has also been demonstrated with different types of particles with varying efficiencies. For example, Johansson et al. have recently reported the use of ultra-small superparamagnetic iron-oxide (USPIO) particles coupled to an RGD peptide sequence to target thrombus, or more specifically GPIIb/IIIa (Johansson, L. O. et al., *J. Mag. Res. Imaging* 2001, 13, 615).

A variety of ligands may be employed for targeting receptors, including but not limited to, monoclonal antibodies, proteins, peptides and small molecules. Monoclonal antibodies, composed of naturally occurring amino acids and their fragments, have been studied extensively for their potential applications in both diagnostics and therapeutics.

For example, Anderson et al. have recently targeted an MRI contrast agent to the $\alpha_v b_3$ integrin using antibody technology to enhance the contrast of angiogenic vessels in vivo (Anderson, S. A. et al., *Mag. Res. Med.* 2000, 44, 433). Though antibodies have a high receptor binding affinity and high specificity, they often demonstrate limited accumulation in the target and relatively slow blood clearance due to their high molecular weight, resulting in only modest target to-background ratios. Peptides are compounds that also contain amino acids (R-amino carboxylic acids) linked by amide (peptide) bonds. Designed by nature for stimulating, inhibiting, or regulating numerous life functions, peptides have been considered ideal agents for therapeutic applications. The difference between proteins and peptides is their sizes. The term "peptides" is usually used to refer to those containing less than 100 amino acids with a molecular weight of about 10,000 Da. Small peptides refer to peptides with less than 30 amino acids or a molecular weight less than 3500 Da. Compared to antibodies or proteins, small peptides offer several advantages. For example, they can tolerate harsher chemical conditions for modification (McAfee, J. G. et al., 1996) or attachment to nano-particles; furthermore, the synthesis of the particle as a whole is simplified and easier to control. Small peptides are also less likely to be immunogenic. Additionally, small peptides are more commonly necessary elements in fundamental biological processes than any other class of molecules, and in many cases the affinities of small peptides for their receptors are significantly greater than those of antibodies or their fragments. Many biologically active peptides, some of them commercially available, provide a suitable starting point. Similarly, other small molecule receptor antagonists such as peptidomimetics may be used as targeting molecules.

Definitions

As used herein, Heat Shock Protein of the embodiments of the invention may be referred to throughout the application as the ligand, the peptide sequence, HSP, the LOX-1 binding peptide, or the binding peptide. Each of these terms are meant to include fragments, fusion peptides, derivatives, variants, and homologues thereof. Further, specific references such as HSP-70 or Seq. Id. Nos. 1-5 are exemplary in nature and also include fragments, fusion peptides, derivatives, variants, and homologues thereof for the specific reference.

A "composition" as used herein, refers broadly to any composition containing a described molecule, peptide, or amino acid sequence. The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g.,sodium dodecyl sulfate (SDS), and other components, e.g., Denhardt's solution, dry milk, salmon sperm DNA, etc.

As used herein, "isolated" will mean material removed from its original environment (e.g., the natural environment in which the material occurs), and thus is "altered by the hand of man" from its natural environment. Isolated material further encompasses an isolated HSP peptide binding sequence or particular HSP70 fragment binding sequence.

The term "fragment" refers to a protein or polypeptide that consists of a continuous subsequence of the subject amino acid sequence and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine.

The term "variant" refers to a protein or polypeptide in which one or more amino acid substitutions, deletions, and/or insertions are present as compared to the subject amino acid sequence and includes naturally occurring allelic variants or alternative splice variants. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 1 below.

TABLE 1

Conservative Amino Acid Substitutions

Basic

Lysine
Histidine
Arginine

Acidic

Aspartic Acid
Glutamic Acid

Uncharged Polar

Asparagine
Serine
Threonine
Tyrosine
Glutamine

Non-Polar

Tryptophan
Cysteine
Glycine
Alanine
Valine
Proline
Methionine
Leucine
Isoleucine
Phenylalanine Table 2 sets out another scheme of amino acid substitution:

TABLE 2

| Original Residue | Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Polypeptides and Variants Thereof

Polypeptides encompasses proteins, peptides and fragments thereof (functional or non-functional) encoded by an HSP nucleotide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type amino acids so derivatized. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide.

In addition, a given protein or polypeptide may contain many types of modifications. Modifications may take place anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, γ-carboxylation of glutamic acid residues, hydroxylation and ADP-ribosylation, selenoylation, sulfation, transfer-RNA mediated addition of amino acids to proteins, such as arginylation, and ubiquitination. PROTEINS—STRUCTURE AND MOLECULAR PROPERTIES, 2nd Ed., T. E. Creighton, W. H. Freeman and Company, New York (1993) and Wold, F., *Posttranslational Protein Modifications: Perspectives and Prospects*, pgs. 1-12 in *Posttranslational Covalent Modification Of Proteins*, H. C. Johnson, Ed., Academic Press, New York (1983); Seifter et al., *Meth. Enzymol.* 182: 626-646 (1990) and Rattan et al., *Protein Synthesis: Posttranslational Modifications and Aging*, Ann. N.Y. Acad. Sci. 663: 48-62 (1992). The term "derivatives" also includes chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of the subject amino acid sequence, as the case may be, as determined by standard methods that are commonly used to compare the similarity in position of the amino acids of two polypeptides. The degree of similarity or identity between two proteins can be readily calculated by known methods, including but not limited to those described in COMPUTATIONAL MOLECULAR BIOLOGY, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carillo H. and Lipman, D., SIAM, *J. Applied Math.*, 48: 1073 (1988). Preferred methods to determine identity are designed to provide the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research*, 12(1): 387 (1984)), BLASTP, BLASTN, and FASTA, Atschul, S. F. et al., *J. Molec. Biol.*, 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.*, 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3× (times) the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure*, vol. 5, supp. 3 [1978] for the PAM250 comparison matrix; see Henikoff et al., *Proc. Natl. Acad. Sci USA*, 89:10915-10919 [1992] for the BLOSUM 62 comparison matrix) also may be used by the algorithm. The percent identity then is calculated by the algorithm. Homologues will typically have one or more amino acid substitutions, deletions, and/or insertions as compared with the comparison subject amino acid, as the case may be.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the subject peptide on which the peptide mimetic is based. As a result of this similar active-site geometry, the peptide mimetic has effects on biological systems that are similar to the biological activity of the subject peptide.

The peptide mimetics of this invention are preferably substantially similar in both three-dimensional shape and biological activity to the subject peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala[1]-Peptide T Binding", Smith C. S. et al., *Drug Development Res.*, 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the subject peptide by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.*, 41:561-566, incorporated herein by reference). According to this modification, the amino acid sequences of the peptides may be identical to the sequences of the subject amino acid sequence, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.*, 41:181-184, incorporated herein by reference in its entirety).

Thus, the amino acid sequences of these peptides may be identical to the sequences of the subject amino acid sequence, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the subject molecules may be replaced with the N-substituted glycine corresponding to the replaced amino acid.

The term "peptide mimetic" or "mimetic" also includes reverse-D peptides and enantiomers. The term "reverse-D peptide" refers to a biologically active protein or peptide consisting of D-amino acids arranged in a reverse order as compared to the L-amino acid sequence of the subject peptide. The term "enantiomer" refers to a biologically active protein or peptide where one or more the L-amino acid residues in the amino acid sequence of a subject peptide is replaced with the corresponding D-amino acid residue(s).

The Binding Moiety—HSP

In one embodiment the Heat Shock Protein may be used in its entirety. More preferably oligomer portions of the HSP are used to bind to cell surface receptors. Therefore, according to one embodiment of the invention, hydrophilic portions of HSP are utilized to make oligomers of 30 or fewer amino acids as they provide better specificity, transport and/or clearance properties. More preferably the HSP used is HSP-70 or an oligomer therefrom.

For each of the recited embodiments the Heat Shock Protein (ligand) may be a full sequence, a fragment thereof, or homologs of either the full sequence, a fragment, or variant thereof. Preferably the Heat Shock Protein is a Heat Shock Protein 70, a fragment thereof, or homologs of either the full sequence, fragment, or variant thereof. More preferably the LOX-1 peptide binding sequences is a HSP-70 fragment.

While in one embodiment HSP-70 may be used in its entirety, certain portions of HSP-70 are more likely to bind to cell surface receptors. In an unaltered state, HSP-70 will have a stable tertiary configuration. However short chained oligomers may either not achieve a stable tertiary state or alternatively not represent a binding portion of the HSP. Therefore, according to one embodiment of the invention, hydrophilic portions of HSP are utilized to make fragments for use in the Complex. Hydrophilic areas provide two distinct advantages: (1) being hydrophilic in nature these shorter chained oligomers are more likely to be stable, and (2) hydrophilic domains are most likely to be responsible for cell binding. The binding moiety may include, for example:

```
DAAKNQVALN PQNTVFDAKR LIGRKFGDPV    (SEQ ID. NO. 1)
VQSDMKHWPF.

QVINDGDKPK VQVSYKGETK AFY.          (SEQ ID. NO. 2)

PEEISSM VLTKMKEIAE AYLGYPVT.        (SEQ ID. NO. 3)

D SQRQATKDAG VIAGLNVLRI INEPTAAAIA  (SEQ ID. NO. 4)
YGLDR.

MGDKSENVQD LLLLDVAPLS LGLETAGGVM.   (SEQ ID. No. 5)

KDNNLLGRFE LSGIPPAPGV PQIEVTFDID.   (SEQ ID. No. 6)
```

According to another embodiment it is preferred to use a segment that is homologous to or larger fragment of SEQ ID Nos. 1-6.

One should recognize that due to the highly conserved nature between HSPs that HSP-70 is exemplary and other HSPs may be utilized. More specifically, it is preferred to use sequences from other HSPs with high homology to the binding regions from HSP-70. Further, the inventors have found that the N-terminal homologous segment is preferred over the C-terminal homologous segment as homology structures suggest there are more hydrophilic domains in the N-terminal half compared to the C-terminal half.

Use of secondary structure analysis show that the N-terminal homologous segment is primarily composed of alpha-helices whereas the C-terminal homologous segment is primarily composed of beta-sheets. Other preferred fragments may be determined through 3-D modeling and surface properties, such as electrostatics and hydrophobics.

For instance, Homologous proteins with experimentally determined structures were identified from the public domain, specifically the Protein Structural Databank, whose sequences showed the highest degree of homology to LOX-1. A phi-psi BLAST search of the PDB structural database was utilized to identify the homologous templates. Subsequently, the crystal structures were obtained from the protein databank.

Further, the following structure information is useful to assist in determining useful sequences and amino acid substitutions therein. The following information is based on an HSP fragment based on 1HJO (human).

1. β-Sheet A
Amino Acid 7-ILE to Amino Acid 28-ILE
Amino Acid 141-ASN to Amino Acid 146-VAL
Amino Acid 168-ASN to Amino Acid 174-ASN 2. β-Sheet B
Amino Acid 42-VAL to Amino Acid 51-ILE 3. Helix 1
Amino Acid 53-ASP to Amino Acid 61-LEU 4. Helix 2
Amino Acid 63-PRO to Amino Acid 65-ASN 5. Helix 3
Amino Acid 70-ALA to Amino Acid 73-LEU 6. Helix 4
Amino Acid 81-PRO to Amino Acid 89-HIS 7. β-Sheet C
Amino Acid 93-GLN to Amino Acid 115-TYR 8. Helix 5
Amino Acid 116-PRO to Amino Acid 135-LEU 9. Helix 6
Amino Acid 152-ASP to Amino Acid 164-ILE 10. Helix 7
Amino Acid 175-GLU to Amino Acid 182-ALA 11. Helix 8
Amino Acid 230-GLY to Amino Acid 248-LYS 12. β-SHEET D
Amino Acid 192-GLU to Amino Acid 337-VAL 13. Helix 9
Amino Acid 257-LYS to Amino Acid 275-SER 14. β-Sheet E
Amino Acid 279-GLN to Amino Acid 298-THR 15. Helix 10
Amino Acid 299-ARG to Amino Acid 323-ASP 16. Helix 11
Amino Acid 328-LYS to Amino Acid 330-GLN 17. Helix 12
Amino Acid 339-GLY to Amino Acid 342-ARG 18. Helix 13
Amino Acid 344-PRO to Amino Acid 353-PHE 19. Helix 14
Amino Acid 368-ALA to Amino Acid 380-LEU Using these parameters, and the methods described herein, several HSP fragments were synthesized. The binding moiety (H) can be represented by a HSP protein, more preferably an HSP-70 protein or fragment thereof so long as it is capable of binding to LOX1.

Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include peptides with additional amino acid residues before or after the subject amino acid sequence on linker peptides. For example, a cysteine residue may be added at both the amino and carboxy terminals of a subject amino acid sequence in order to allow the cyclization of the subject amino acid sequence by the formation of a di-sulphide bond. The term "variant" also encompasses polypeptides that have the subject amino acid sequence with at least one and up to 25 or more additional amino acids flanking either the 3' or 5' end of the subject amino acid.

Signaling Moieties

Throughout this description, the phrase "S provides a signal that can be detected in vivo or detected in vitro" denotes an entity that can be imaged by itself or by reacting with another substance, and that can be detected in vivo or in vitro by a detection apparatus. More specifically, the labeling entities S include enzymes, fluorescent materials, chemiluminescent materials, biotin, avidin, radioisotopes, radionuclides, X-ray imaging agents, MRI contrast agents, ultrasonography imaging elements, paramagnetic materials, and the like. It should be recognized that for each embodiment of the invention, S may be independently selected from a luminescent dye, a radionuclide, a near infrared dye, a magnetically active isotope, a superparamagnetic particle, a metal ion having a Z value of greater than 50, an encapsulated species, and combinations thereof. Similarly, the below listed signaling agents may be used alone or in combination for each of the recited embodiments.

Any signal moiety/source can be used so long as it is capable of binding the HSP moiety and generating a detectable signal. Suitable signal moieties include a luminescent dye, a radionuclide, a near infrared dye, a magnetically active isotope, a superparamagnetic particle, a metal ion having a Z value of greater than 50, an encapsulated species such as micelles, liposomes, polysomes, and gas-filled microbubles, and a combination thereof.

The signal moiety may include, for example:

dyes, fluorescent dye, chemiluminescent dyes for optical imaging, histology;

molecules containing high-Z elements, such as iodine or bismuth, for X-ray imaging, computed tomography (CT);

gas-filled microbubbles, fluorocarbon filled micelles for ultrasonography (US);

paramagnetic ions, such as chelated $Gd^{+++}$, or superparamagnetic particles such as superparamagnetic iron oxide nanoparticles (SPIO) for magnetic resonance imaging (MRI); or radionuclides such as 99mTc for single photon emission computed tomography (SPECT) or $^{18}F$ for positron emission tomography (PET).

Particularly preferred signal moieties include fluorescein, $^{11}C$, $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94m}Tc$, $^{94}Tc$, $^{99m}Tc$, 111In, $^{123}I$, $^{124}I$, $^{125}I$, $^{131}I$, $^{154-158}Gd$ and $^{175}Lu$, superparamagnetic iron oxide nanoparticles, heavy metal ions, gas-filled microbubbles, optical dyes, porphyrins, texaphyrins, highly iodinated organic compounds chelates thereof, polymers containing at least one of the aforementioned components, endoedral fullerenes containing at least one of the aforementioned, and mixtures thereof. Even more preferably, the signal moieties are $^{18}F$ for PET, superparamgnetic iron oxide nanoparticles (SPIO) for MRI, chelated Gd, I, and Y. Most preferably, the signal moiety is $^{18}F$ for PET.

$^{18}F$-Fluoride can be obtained from cyclotrons after bombardment of $^{18}O$-enriched water with protons. Typically, the enriched water containing $^{18}F$-fluoride is treated with a base having a counter-ion that is any alkali metal cation ($M^+$), such as potassium or another monovalent ion as well as a chelate for $M^+$, such as Kryptofix 222. The water can be evaporated off to produce a residue of chelate M-$^{18}F$, which can be taken up in an organic solvent for further use. The purpose of the chelate is to solubilize the M-18F in the organic solvent and confer nucleophilicity to the $^{18}F$-fluoride. Instead of a chelate and $M^+$, a quaternary ammonium salt, phosphonium salt or guandinium may be used to solubilize the $^{18}F$-fluoride in the organic solvent and confer nucleophilic reactivity to the $^{18}F$-fluoride. Potassium is generally used as a counter-ion Because fluoride is the most electronegative element, it has a tendency to become hydrated and lose its nucleophilic character. To minimize this, the labeling reaction preferably is performed under anhydrous conditions. For example, fluoride (as potassium fluoride or as a complex with any of the other counter-ions discussed above) can be placed in organic solvents, such as acetonitrile or THF. With the assistance of agents that bind to the counter-ion, such as Kryptofix 2.2.2 (4,7,13,16,21,24-hexaoxa-1,10-diazabicyclo[8.8.8]-hexacosane), the fluoride ion is very nucleophilic in these solvents. The remaining portion of the chelate molecule of embodiments of the invention then can be added to the solvent and the chelate thereby labeled with the $^{18}F$. Using the guidelines provided herein, those skilled in the art are capable of labeling the ligands of the present invention with $^{18}F$. Alternatively, labeling may be accomplished through the use of $^{18}F-F_2$ or electrophilic fluorinating agents derived from $^{18}F-F_2$.

In a more preferred embodiment the signaling source is positron emitting radioisotopes $^{18}F$, $^{11}C$ and $^{64}Cu$ (for PET); gamma emitting radioisotopes $^{99m}TC$ (for PET); and contrast agents for MR, particularly, multiple Gd nuclei.

Linking Agents

L includes any moiety that is capable of connecting the signal moiety S or therapeutic agent T to the HSP moiety (H). For each of the described embodiments L may be independently selected. For instance, the linker may an organic radical having a valence of at least 2, a metal chelating agent that binds at least one metal cation, metal chelating agent.

In certain cases, such as with signaling agents, such as $^{18}F$ or $^{11}C$ a linker may not be necessary to connect the signaling agent or therapeutic. Similarly, a radioisotope can be directly attached to H via a covalent bond. In many cases it is preferred to include L in order to attach S to H or T to H. That is, n in the equation for the molecule of embodiments of the invention is 1. Preferred linking agents include polypeptides, proteins, and small organic moieties. For example, lysine-glycine analogs, derivatives and variants can be used, conventional chelators such as cyclohexyl alanine, DTPA, 1,4,7-triaza-cyclononane-N,N',N"-triacetic acid (NOTA), p-bromoacetamido-benyl-tetraethylaminetetraacetic acid (TETA), 1,4,7,10-tetraazacyclododecanetetraacetic acid (DOTA), and combinations thereof. A preferred linking agent could be a lysine-glycine derivative such as KKGG Organic moieties having a valence of at least 2 are useful as L, including small organic moieties such as benzoate or propionate (FIG. 4). The organic radical may be covalently bound to both S and H or T and H, or it may be ionically bound to S, T, H, or both S and H or T and H. The organic moiety suitable for use as the linking agent typically has from about 1 to about 10,000 carbon atoms, and may include, an organic radical selected from the group consisting of alkylene, arylene, cycloakylene, aminoaklylene, aminoarylene, aminocycloalkylene, thioalkylene, thioarylene, thiocycloalkylene, oxyalkylene, oxyarylene, oxycycloalkylene, acylalkylene, acylarylene, acylcycloalkylene units, and combinations thereof. A particularly preferred acylarylene unit is a 4-acylphenylene group having the structure below:

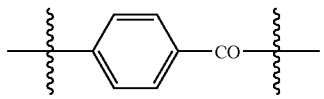

Other suitable linking agents including metal chelating agents, such as one or more of DTPA, 1,4,7-triaza-cyclononane-N,N',N"-triacetic acid (NOTA), p-bromoacetamido-benyl-tetraethylaminetetraacetic acid (TETA), 1,4,7,10-tetraazacyclododecanetetraacetic acid (DOTA), EDTA, and CHXa. It is preferred that the metal chelating agents be capable of binding to at least one metal selected from cations of $_{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, 154-158Gd, and 175Lu.

As appreciated by those skilled in the art, various linking agents are used with certain signal moieties. For example, signal generating moieties, such as $^{64}$Cu, typically require a linking ligand, whereas $^{18}$F does not. In addition, labeled prosthetic groups such as $^{18}$F-fluoropropionate or $^{18}$F-fluorobenzoate (FIG. 4) can be used such that, once prepared, they can be conjugated to the peptide via active ester conjugation. Those skilled in the art are capable of synthesizing a suitable linking agent, if needed, together with a suitable signaling moiety, using the guidelines and synthesis techniques provided herein.

Methods of synthesizing peptidic ligand linkers (L) that are useful in labeling moieties (H) that recognize LOX-1, as well as methods of directly labeling binding agents that bind LOX-1 are described hereinafter.

Peptide Synthesis

Peptides were synthesized using standard solid phase techniques with $N^{\alpha}$-Fmoc-protected amino acids using 2,4-dimethoxybenzhydrylamine resin (Rink Amide AM) on a 25 μmole scale (Fmoc=Fluorenylmethoxycarbonyl). The peptides were synthesized using a Rainin/Protein Technology Symphony solid phase peptide synthesizer (Woburn, Mass.). Prior to any chemistry, the resin was swelled for one hour in methylene chloride, and subsequently exchanged out with DMF (dimethylformamide) over half-hour or more. Each coupling reaction was carried out at room temperature in DMF with five equivalents of amino acid. Reaction times were typically 45 minutes, 1 hour for residues that were expected to be difficult to couple (for example, coupling Isoleucine, I, to proline, P, in the IPP sequence). The coupling reagent used was HBTU (O-Benzotriazolyl-1-yl-N,N,N',N'-tetramethyluronium hexafluorophosphate), with NMM (N-methylmorpholine) as the base. For each step the coupling agent was delivered at a scale of five equivalents relative to the estimated resin capacity, and reaction carried out in 2.5 ml of 0.4 M NMM solution in DMF. The reactions did not perturb the side-chains of the amino acids, which were typically protected with acid labile groups if reactive groups were present. Generally, the tyrosine, threonine and serine side chains were protected as the corresponding tert-butyl ethers. The glutamic acid side chain was protected as the corresponding tert-butyl ester. The lysine and ornithine side chains were Boc protected. The glutamine side chain was protected as the y-triphenylmethyl derivative, and the arginine side chain was protected as the 2,2,5,7,8-Pentamethyl-chromane-6-sulfonyl derivative.

Following each coupling reaction, the N-terminal Fmoc-protected amine was deprotected by applying 20% piperidine in DMF twice at room temperature for approximately 15 minutes. After the addition of the last residue the resin, still on the peptide synthesizer, was rinsed thoroughly with DMF and methylene chloride.

The invention used a cocktail consisting of 1 mL TFA, 2.5% TSP (triisopropylsilane) and 2.5% water to cleave the peptides from the resin. The resin and cocktail were stirred at room temperature for approximately 3 to 4 hours. The resin beads were filtered off using glass wool, followed by rinsing with 2-3 ml of TFA. The peptide was precipitated with 40 ml of ice-cold ether and centrifuged at 3000-4000 rpm until the precipitate formed a pellet at the bottom of the centrifuge tube. The ether was decanted, and the pellet was resuspended in cold ether (40 mL) and centrifuged again; the process was repeated two to three times. During the final wash 10 ml of Millipore water was added to 30 ml of cold ether, and the mixture was centrifuged again. The ether was decanted. The aqueous layer, containing the crude peptide, was transferred to a round bottom flask for lyophilization.

The synthesis of the peptides was confirmed by mass spectrometry using Time-of-Flight Matrix assisted Laser Desorption Spectroscopy (MALDI-TOF). Preliminary LC/MS techniques were also used to further characterize the pure product amidst the crude synthetic mixture.

Linkage Synthesis

Coupling the fluorescein dye, 5(6)-carboxyfluorescein, to the N-terminus of a synthesized peptide, preferably included adding the dye, HBTU and NMM preferably to the resin in the same manner as the amino acids described above. After the reaction, the resin preferably is thoroughly washed with DMF and methylene chloride and dried under a stream of nitrogen. A mixture containing 1 mL TFA, 2.5% TSP (triisopropylsilane) and 2.5% water can be used to cleave the peptides from the resin. The resin and mixture preferably are stirred at room temperature for approximately 3 to 4 hours. The resin beads then can be filtered off using glass wool, followed by rinsing with 2-3 ml of TFA. The peptide then preferably is precipitated with ice-cold ether (40 mL) and centrifuged (e.g., at 3000-4000 rpm) until the precipitate formed a pellet at the bottom of the centrifuge tube. The ether can be decanted, and the pellet resuspended in cold ether (40 mL) and centrifuged again—the process can be repeated two to three times. During the final wash, 10 ml of Millipore water preferably is added to 30 ml of cold ether, and the mixture was centrifuged again. The ether then can be decanted, the aqueous layer containing the crude peptide then can be transferred to a round bottom flask for lyophilization. Crude yields for peptide synthesis were usually approximately 90%. No unlabeled peptide was typically observed.

Peptides preferably are purified by reverse phase semi-preparative or preparative HPLC with a C4-silica column (Vydac, Hesperia, Calif.). The peptide chromatograms can be monitored at 220 nm, which corresponds to the absorption of the amide chromophore. Monitoring at 495 nm also can be observed to ensure the presence of the fluorescein dye on the peptide. It is preferred to use a solvent system including $CH_3CN$/TFA (acetonitrile/Trifluoroacetic acid; 100:0.01) and $H_2O$/TFA (water/Trifluoroacetic acid; 100:0.01) eluents at flow rates of 3 ml/min and 10 ml/min for semipreparative and preparative, respectively. Dissolved crude peptides in Millipore water can be injected at a scale of 1.5 mg and 5-10 mg peptide for semipreparative or preparative, respectively. The chromatogram shape was analyzed to ensure good resolution and peak shape. Gradient conditions for all peptides were typically 5 to 50% of CH₃CN/TFA (100:0.01) in 30 minutes. Purified peptide identity was confirmed by matrix-assisted laser desorption time-of-flight mass spectroscopy.

Therapeutics

Therapeutics useful for attachment and internalization are not limited. The pharmaceutical compounds or compositions and biologically active compositions may, for example, include antibiotics, analgesics, vaccines, antiinflammatory agents, antidepressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, and steroids, compositions to promote growth such as hormones, or other growth stimulating agents, mixtures thereof, and the like.

Active components may be selected from any known active material that would provide improved efficacy if it were internalized into a cell, such as anti-cancer agents. Active components may include, for example, antimetabolites such as 5-flurouracil (5-FU), cytosine arabinoside (ARAc), 6-mercaptopurine, methotrexate; aklylating agents such as nitrogen mustard, cyclophosphamide, nitrosoureas, cis-platin; plant alkaloids such as vincristine, vinblastine, etoposide (VP16); antibiotics such as mitomycin C, bleomycin, doxorubicin; or hormones such as tamoxifen, flutamide.

Preferred embodiments of the invention now will be explained with reference to the following non-limiting examples.

EXAMPLES

Each of the below examples are prophetic examples.

Example 1

(H) will be covalently attached through a 4-acylphenylene group (L) to flourescein (S) using standard techniques known in the art. The ability of the complex to bind to cells will be tested using a cell line. The complex will be incubated with the cells and then washed. The cells will then be imaged using standard techniques.

Additionally, the ability of HSP fragments to internalize the signal will be demonstrated through the realization of the dye internalized to the cell as opposed to being on the cell surface as demonstrated through fluorescence imagery. Fragments will be tagged with pH sensitive dyes such as CypHer (Amersham Biosciences, Pscataway, N.J.) that will fluoresce upon internalization into cells.

Example 2

(H) will be covalently attached through Lys-Lys-Gly-Gly (L) to $^{18}$F (S) using standard techniques known in the art. The complex will then be delivered in vivo through injection to 5 control and five diseased ApoE−/− mice, available from Jackson Laboratories. Following delivery the mouse will be scanned using standard PET techniques. The diseased mouse will show specific binding along affected arterial walls.

In a second stage, the treatment with the complex will be repeated to illustrate the build up of imaging agent allowing for greater resolution of affected areas.

Example 3

(H) will be covalently attached through DTPA (L) to taxol (T) using standard techniques known in the art. The ability of the complex to bind to cells will be tested using a cell line. The complex will be incubated with the cells and then washed. The ability of HSP fragments to internalize the signal will be demonstrated through the realization of the dye internalized to the cell as opposed to being on the cell surface as demonstrated through fluorescence imagery.

Example 4

(H) will be covalently attached through $^{68}$Ga (L) using standard techniques known in the art. The complex will then be delivered in vivo through injection to 5 control and five diseased ApoE−/− mice. Following delivery the mouse will be scanned using standard PET techniques. The diseased mouse will show specific binding along affected arterial walls.

In a second stage, the treatment with the complex will be repeated to illustrate the build up of imaging agent allowing for greater resolution of affected areas.

Example 5

(H) will be covalently attached through Lys-Lys-Gly-Gly (L) to $^{18}$F (S) and further covalently linked to taxol (T) using standard techniques known in the art. The ability of the complex to bind to cells will be tested using heat-shocked HeLa cell line and unstressed normal HeLa cells. Further the complex will be incubated with the cells and then washed. The cells expressing LOX-1 will show greater selective cell death. The selectivity of the cell death will be further illustrated through imaging of the cells and internalization of the signal.

Example 6

As an example of the complex without a linker, (H) will be covalently attached through $^{68}$Ga (S) using standard techniques known in the art. The complex will then be delivered in vivo through injection to 5 control and five diseased ApoE−/− mice. Following delivery the mouse will be scan using standard PET techniques. The diseased mouse will show specific binding along affected arterial walls.

In a second stage, the treatment with the complex will be repeated to illustrate the build up of imaging agent allowing for greater resolution of affected areas.

Embodiments of the invention have been described with reference to specific embodiments and examples. Those skilled in the art appreciate that various modifications may be made to embodiments of the invention without departing from the spirit and scope thereof.

What is claimed is:

1. A compound having the formula $S-(L)_n-H$ wherein S is a signal moiety selected from the group consisting of a luminescent dye, a near infrared dye, a paramagnetic ion, a superparamagnetic particle, $^{11}$C, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{154}$-$^{158}$Gd, and $^{175}$Lu, L links S to H, wherein L is a linker selected from the group consisting of a covalent bond, polypeptide, protein, organic radical having a valence of at least 2, and chelating agent, H is HSP-70, or a fragment thereof that binds to LOX-1, and n is either 0 or 1.

2. A composition, comprising:

a compound having the formula $S-(L)_n-H$ disposed in a pharmaceutically acceptable excipient, wherein S is a signal moiety selected from the group consisting of a luminescent dye, a near infrared dye, a paramagnetic ion, a superparamagnetic particle, $^{11}$C, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{111}$In, $^{154}$-$^{158}$Gd, and $^{175}$Lu, L links S to H, wherein L is a linker, H is HSP-70, or a fragment thereof that binds to LOX-1, and n is either 0 or 1.

3. The compound of claim 1, wherein the luminescent dye is fluorescein.

4. The compound of claim 1, wherein the paramagnetic ion is an isotope of gadolinium.

5. The compound of claim 1, wherein the superparamagnetic particle is a nanoparticle.

6. The compound according to claim 5, wherein the nanoparticle comprises at least one of iron oxide and elemental iron.

7. The compound according to claim 1, wherein the organic radical is covalently bound to both S and H.

8. The compound according to claim 1, wherein the organic radical is ionically bound to one of S and H.

9. The compound according to claim 1, wherein the organic radical is ionically bound to both S and H.

10. The compound according to claim 1, wherein the organic radical comprises between 1 and about 10,000 carbon atoms.

11. The compound according to claim 1, wherein the organic radical is selected from the group consisting of alkylene, arylene, cycloakylene, aminoaklylene, aminoarylene, aminocycloalkylene, thioalkylene, thioarylene, thiocycloalkylene, oxyalkylene, oxyarylene, oxycycloalkylene, acylalkylene, acylarylene, acylcycloalkylene units, and combinations thereof.

12. The compound of claim 11, wherein the acylarylene unit is a 4-acylphenylene group having the following structure:

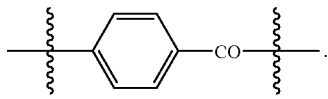

13. The compound of claim 1, wherein the L is a metal chelating agent.

14. The compound according to claim 13, wherein the metal chelating agent binds at least one metal cation selected from the group consisting of cations of $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{154}$-$^{158}$Gd, and $^{175}$Lu.

15. The compound of claim 13, wherein the metal chelating agent is selected from the group consisting of diethylene triamine pentaacetic acid (DTPA), 1,4,7-triaza-cyclononane-N,N',N''-triacetic acid (NOTA), p-bromoacetamido-benyl-tetraethylaminetetraacetic acid (TETA), 1,4,7,10-tetraazacyclododecanetetraacetic acid (DOTA), ethylenediaminetetraacetic acid (EDTA), CHXA ({N-[2-amino-3-(p-isothiocyanatophenyl)]trans-cyclohexane-1,2-diaminen ,N,N',N'',N''',N''''-pentaacetic acid}).

16. The compound according to claim 1, wherein H is an N-terminus fragment of Heat Shock Protein 70.

17. A kit comprising the composition of claim 2.

* * * * *

UNITED STATES PATENT AND TRADEMARK OFFICE
CERTIFICATE OF CORRECTION

PATENT NO. : 7,575,738 B2
APPLICATION NO. : 10/917326
DATED : August 18, 2009
INVENTOR(S) : Syud et al.

It is certified that error appears in the above-identified patent and that said Letters Patent is hereby corrected as shown below:

On the Title Page, in Item (75), under "Inventors", in Column 1, Line 2, delete "Clifton," and insert -- Clifton Park, --, therefor.

On the Title Page, in Item (75), under "Inventors", in Column 1, Line 3, delete "Clifton," and insert -- Clifton Park, --, therefor.

Title Page on Page 2, in Item (56), under "OTHER PUBLICATIONS", in Column 1, Line 13, delete "19963," and insert -- 1993, --, therefor.

Title Page on Page 2, in Item (56), under "OTHER PUBLICATIONS", in Column 2, Line 13, delete "Muclear" and insert -- Nuclear --, therefor.

Title Page on Page 2, in Item (56), under "OTHER PUBLICATIONS", in Column 2, Line 15, delete "Dymanic" and insert -- Dynamic --, therefor.

In Column 1, Line 64, delete "Chemisfry," and insert -- Chemistry, --, therefor.

In Column 10, Lines 30-31, delete "111In, 154-158Gd," and insert -- $^{111}$In, $^{154\text{-}158}$Gd, --, therefor.

In Column 19, Line 59, delete "$^{52}$Fe" and insert -- $^{52}$Fe, --, therefor.

In Column 19, Line 60, delete "111In," and insert -- $^{111}$In, --, therefor.

In Column 20, Line 12, delete "M-18F" and insert -- M-$^{18}$F --, therefor.

In Column 21, Line 24, delete "$_{52}$Fe," and insert -- $^{52}$Fe, --, therefor.

In Column 21, Line 25, delete "154-158Gd, and 175Lu." and insert -- $^{154\text{-}158}$Gd, and $^{175}$Lu. --, therefor.

In Column 22, Line 1, delete "y-triphenylmethyl" and insert -- γ-triphenylmethyl --, therefor.

In Column 27, Line 26, in Claim 1, delete "$^{154\text{-}158}$Gd," and insert -- $^{154\text{-}158}$Gd, --, therefor.

In Column 27, Line 41, in Claim 2, delete "$^{111}$In, $^{154\text{-}158}$Gd," and insert -- $^{99m}$Tc, $^{111}$In, $^{154\text{-}158}$Gd, --, therefor.

CERTIFICATE OF CORRECTION (continued)
U.S. Pat. No. 7,575,738 B2

In Column 28, Line 40, in Claim 13, after "wherein" delete "the".

In Column 28, Line 54, in Claim 15, delete "isothiocyanatophenyl)]trans" and insert -- isothiocyanatophenyl)propyl]-trans --, therefor.

In Column 28, Line 55, in Claim 15, delete "diaminen ,N," and insert -- diamine-N, --, therefor.

Signed and Sealed this

Sixteenth Day of February, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 40
<212> TYPE: PRT
<213> ORGANISM: Artificial sequence

```
<220> FEATURE:
<223> OTHER INFORMATION: Synthetic Carrier

<400> SEQUENCE: 1

Asp Ala Ala Lys Asn Gln Val Ala Leu Asn Pro Gln Asn Thr Val Phe
1               5                   10                  15

Asp Ala Lys Arg Leu Ile Gly Arg Lys Phe Gly Asp Pro Val Val Gln
                20                  25                  30

Ser Asp Met Lys His Trp Pro Phe
            35                  40

<210> SEQ ID NO 2
<211> LENGTH: 23
<212> TYPE: PRT
<213> ORGANISM: Artificial sequence
<220> FEATURE:
<223> OTHER INFORMATION: Synthetic carrier

<400> SEQUENCE: 2

Gln Val Ile Asn Asp Gly Asp Lys Pro Lys Val Gln Val Ser Tyr Lys
1               5                   10                  15

Gly Glu Thr Lys Ala Phe Tyr
            20

<210> SEQ ID NO 3
<211> LENGTH: 25
<212> TYPE: PRT
<213> ORGANISM: Artificial sequence
<220> FEATURE:
<223> OTHER INFORMATION: Synthetic carrier

<400> SEQUENCE: 3

Pro Glu Glu Ile Ser Ser Met Val Leu Thr Lys Met Lys Glu Ile Ala
1               5                   10                  15

Glu Ala Tyr Leu Gly Tyr Pro Val Thr
            20                  25

<210> SEQ ID NO 4
<211> LENGTH: 36
<212> TYPE: PRT
<213> ORGANISM: Artificial sequence
<220> FEATURE:
<223> OTHER INFORMATION: Synthetic carrier

<400> SEQUENCE: 4

Asp Ser Gln Arg Gln Ala Thr Lys Asp Ala Gly Val Ile Ala Gly Leu
1               5                   10                  15

Asn Val Leu Arg Ile Ile Asn Glu Pro Thr Ala Ala Ala Ile Ala Tyr
                20                  25                  30

Gly Leu Asp Arg
        35

<210> SEQ ID NO 5
<211> LENGTH: 30
<212> TYPE: PRT
<213> ORGANISM: Artificial sequence
<220> FEATURE:
<223> OTHER INFORMATION: Synthetic carrier

<400> SEQUENCE: 5

Met Gly Asp Lys Ser Glu Asn Val Gln Asp Leu Leu Leu Leu Asp Val
1               5                   10                  15

Ala Pro Leu Ser Leu Gly Leu Glu Thr Ala Gly Gly Val Met
```

```
-continued
                         20              25              30

<210> SEQ ID NO 6
<211> LENGTH: 29
<212> TYPE: PRT
<213> ORGANISM: Artificial sequence
<220> FEATURE:
<223> OTHER INFORMATION: Synthetic carrier

<400> SEQUENCE: 6

Lys Asp Asn Asn Leu Leu Gly Arg Phe Glu Leu Ser Gly Ile Pro Pro
1               5                   10                  15

Ala Pro Gly Val Pro Ile Glu Val Thr Phe Asp Ile Asp
            20                  25
```